(12) United States Patent
Levin et al.

(10) Patent No.: US 7,425,211 B2
(45) Date of Patent: Sep. 16, 2008

(54) CRYOGENIC PROBE FOR TREATING ENLARGED VOLUME OF TISSUE

(75) Inventors: Alexander Levin, Binyamina (IL); Didier Toubia, Raanana (IL)

(73) Assignee: Arbel Medical Ltd., Yokneam (IL)

( * ) Notice: Subject to any disclaimer, the term of this patent is extended or adjusted under 35 U.S.C. 154(b) by 113 days.

(21) Appl. No.: 11/462,244

(22) Filed: Aug. 3, 2006

(65) Prior Publication Data

US 2008/0033414 A1 Feb. 7, 2008

(51) Int. Cl.
*A61B 18/02* (2006.01)

(52) U.S. Cl. .......................................... 606/20; 606/23

(58) Field of Classification Search ............. 606/20–28; 607/88, 89
See application file for complete search history.

(56) References Cited

U.S. PATENT DOCUMENTS

| | | | | |
|---|---|---|---|---|
| 5,281,215 A | * | 1/1994 | Milder | 606/20 |
| 5,885,276 A | * | 3/1999 | Ammar et al. | 606/21 |
| 6,565,556 B1 | * | 5/2003 | Korpan et al. | 606/23 |
| 6,772,766 B2 | * | 8/2004 | Gallo et al. | 128/898 |
| 6,913,604 B2 | * | 7/2005 | Mihalik et al. | 606/22 |
| 6,942,659 B2 | | 9/2005 | Lehmann | |
| 6,951,569 B2 | | 10/2005 | Nohilly | |
| 6,954,977 B2 | | 10/2005 | Maguire | |
| 6,995,493 B2 | | 2/2006 | Isoda | |
| 7,001,378 B2 | | 2/2006 | Yon | |
| 7,025,767 B2 | | 4/2006 | Schaefer | |
| 2005/0177147 A1 | | 8/2005 | Vancelette | |

* cited by examiner

*Primary Examiner*—Ahmed M Farah
(74) *Attorney, Agent, or Firm*—Heslin Rothenberg Farley & Mesiti P.C.

(57) ABSTRACT

The invention proposes a cryoprobe for surgical and other treatments. The cryoprobe comprises a bellow-wise section that performs displacement of a distal cryotip forwards with elevation of operation pressure in the interior of the cryoprobe. Needle-wise metal elements are installed on the external side of the cryotip. These needle-wise elements are deflecting outwards by a deflecting member fastened on the distal edge of an external shaft of the cryoprobe. This allows to enlarge significantly a frozen volume of the treated tissue for same operation temperature and the outer diameter of the cryoprobe.

14 Claims, 6 Drawing Sheets

CRYOGENIC PROBE FOR TREATING ENLARGED VOLUME OF TISSUE

BACKGROUND OF THE INVENTION

1. Field of the Invention

The present invention is directed to providing a cryogenic probe for medical applications, such as surgery.

2. Summary Of the Prior Art

Cryogenic technology provides cooling to very low temperatures. It is widely used in medicine, and particularly in surgery. Freezing tissue can kill its cells, and this makes cryosurgery particularly useful for treating cancerous growths. A cryogenic-probe may be used to kill the cells of malignant cysts in mammary tissue. The cryoprobe is required to have a small diameter to cause minimal damage and trauma to the body tissue in its passage through body tissue.

Typically, the site requiring treatment is significantly larger than the diameter of the cryoprobe and is all too frequently wider than the effectively frozen volume of tissue that is treatable by a single probe insertion. Use of multiple probes causes additional trauma and discomfort. Indeed, it will be appreciated that resorting to such procedures will invariably cause trauma to a large volume of tissue contacted along the entire length of the cryogenic probe used to bring the probe tip to its destination.

One interesting development that addresses the issue of treating a considerably larger volume of tissue than that in proximity to the shaft of the ablation needle is described in U.S. Pat. No. 7,025,767 to Schaefer et a., titled "Tumor ablation needle with independently activated and independently traversing tines" which relates to a tumor ablation needle for use to treat ablated tumors with RF energy. The tumor ablation needle described therein comprises a needle with a spreading array of individually traversing conductive tines that are independently positioned. Specifically, An ablation probe, comprising: an elongated member having an exterior wall, a proximal end, and a distal end; a plurality of electrical insulators extending through the elongated member, each of the insulators having a lumen, wherein the elongated member has apertures extending along the exterior wall into each of the electrical insulators; a plurality of elongated electrode tines extending through the respective insulator lumens; and a plurality of side members associated with the proximal end of the elongated member, the side members mechanically connected to the respective electrode tines through the respective apertures for being operable to independently move the respective electrode tines to extend beyond, or retract within, the distal end of the elongated member, is discussed.

There are some US patents teaching designs of cryosurgical probes or catheters with variable shapes of their distal tips. These include U.S. Pat. Nos. 7,001,378, 6,954,977, 6,951,569, 6,942,659, 6,913,604, 6,995,493. Such patents can be divided into three categories:

1. Cryocatheters with inflatable cryotips.
2. Cryoprobes or cryocatheters with tubular spiral-wise cryotips.
3. Cryoprobes with linearly extending cryotips.

U.S. Patent application No. 20050177147 describes a cryoablation system which includes an elongated tubular cannula having a proximal end, a distal end, and a longitudinal axis, an expandable balloon extending from the distal end of the cannula and fluidly connected to a source of heat transfer fluid by at least one fluid path, a pump for circulating the heat transfer fluid into and out of the balloon, a probe handle coupled to the proximal end of the cannula and in fluidic communication with the balloon through the cannula, and a heat exchanger for varying the temperature of the heat transfer fluid, wherein the heat exchanger is fluidly connected to a secondary refrigerant source. The balloon is preferably expandable in response to an addition of a volume of heat transfer fluid. The heat exchanger may be positioned within the probe handle so that the secondary refrigerant can cool the heat transfer fluid to a treatment temperature before the heat transfer fluid is provided to the balloon, or the heat exchanger may alternatively be positioned within the console of the system so that the secondary refrigerant can cool the heat transfer fluid to a treatment temperature before the fluid is provided to the probe handle, or the heat exchanger may alternatively be positioned within the cannula so that the secondary refrigerant can cool the heat transfer fluid to a treatment temperature before the heat transfer fluid is provided to the balloon. In another alternative, the heat exchanger is positioned at least partially within the balloon.

However, there is no design of a cryoprobe or cryocatheter, which allows to enlarge significantly an ice ball formed around the cryotip without inflating this cryotip and without substantial increase of the effective diameter of the cryotip.

There is a need for a narrow cryogenic probe that can treat a relatively large volume of tissue, and the present invention addresses this need.

SUMMARY OF THE INVENTION

In a first aspect, the present invention is directed to providing a cryogenic probe for coupling via a cryogenic conduit to a cryogenic cooling system. The cryogenic probe comprises three concentric lumen: an outer lumen ending in a perforated tip having at least one aperture there through and an inner deflecting member; an intermediate lumen that terminates at distal end thereof in a closed bellows arrangement to which a needle array is coupled, and is sealingly connected at proximal section thereof to the outer lumen; and an inner lumen that is open ended and serves to bring a cryogen into close proximity with the distal end of the intermediate lumen; such that boiling and expansion of the cryogen in the inner lumen causes the bellows arrangement to expand, forward with displacement of the needle arrangement forwards towards the perforated tip, such that deflecting member deflects at least one flexible needle of the needle array, sideways and outwards through at least one aperture, to protrude outwards from the distal end of the cryogenic probe.

The cryogenic probe may be used for medical applications such that displacement the needle array forwards by expansion of the bellows causes at least one needle to be deflected by the deflecting member and to protrude outwards from the outer lumen, allowing treatment of tissue in a larger volume.

In preferred embodiments, the needle array comprises a plurality of flexible needles arranged in a regular polygon array, said at least one aperture comprises a plurality of apertures such that displacement of the needle array forwards in the cylinder causes the plurality of flexible needles to splay, by them being deflected sideways and outwards through the at least one aperture to protrude outwards from the distal end of the cryogenic probe.

Typically, the plurality of flexible needles comprises needles that are identical with each other.

Optionally, at least one flexible needle is a solid needle; the proximal end thereof being cryogenically cooled, thereby cooling the distal end thereof by thermal conduction.

Alternatively, at least one flexible needle is a hollow needle having an open proximal end and a closed distal end; the hollow needle being cryogenically cooled by a cryogen therein. Preferably, the inner surface of such a hollow needle is at least partially coated with an open-pore porous metal coating.

The outer lumen is preferably characterized by at least one of the following list of restrictions: (i) a high rigidity and (ii) a thermal insulation means.

The deflecting member is preferably characterized by at least one of the following list of restrictions: (a) the deflecting member is fabricated at least partially from a metal having a high thermal conductivity coefficient; (b) an inner surface of the deflecting member having a shape suitable for smoothly deflecting at least one flexible needle.

Optionally the bellows head further comprises an internal porous coating having open pore porosity providing a surface for boiling cryogen thereupon.

Optionally, the inner lumen is a cryogenic conduit that includes an expansion orifice at distal end thereof to allow a high pressure cryogenic gas to expand into the intermediate lumen and to partially liquefy.

Optionally, the cryogenic cooling system uses a liquid cryogen.

Optionally, the cryogenic probe tip further comprises an additional needle extending coaxially from the distal end of the bellows head on the intermediate lumen; the deflecting member having an axial hole there through to allow passage of the additional needle.

BRIEF DESCRIPTION OF THE FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawings making apparent to those skilled in the art how the several forms of the invention may be embodied in practice.

In the accompanying drawings.

DESCRIPTION OF THE PREFERRED EMBODIMENTS

The present invention relates to novel cryogenic probes that are useful for a variety of medical applications, particularly surgical techniques such as cryoablation.

Such probes are useful for treating cysts and cancerous growths and, to be directed to a desired location, have to pass through healthy body tissue or through body cavities, and, to minimize trauma to healthy tissue, should be as narrow as possible. To effectively treat a cancerous growth, the volume of cryogenically frozen tissue should include all the cancerous cells. Thus it is desired that the effective diameter of the active part of the probe tip should be large. These are competing requirements.

The volume treatable by a single insertion of a single, acceptably narrow probe of the prior art may be insufficient to treat the full volume of tissue requiring treatment. The present invention provides a extendible probe tip, that is preferable configurable to extend sideways as necessary, between fully extended and fully retracted limits.

Figure 1:
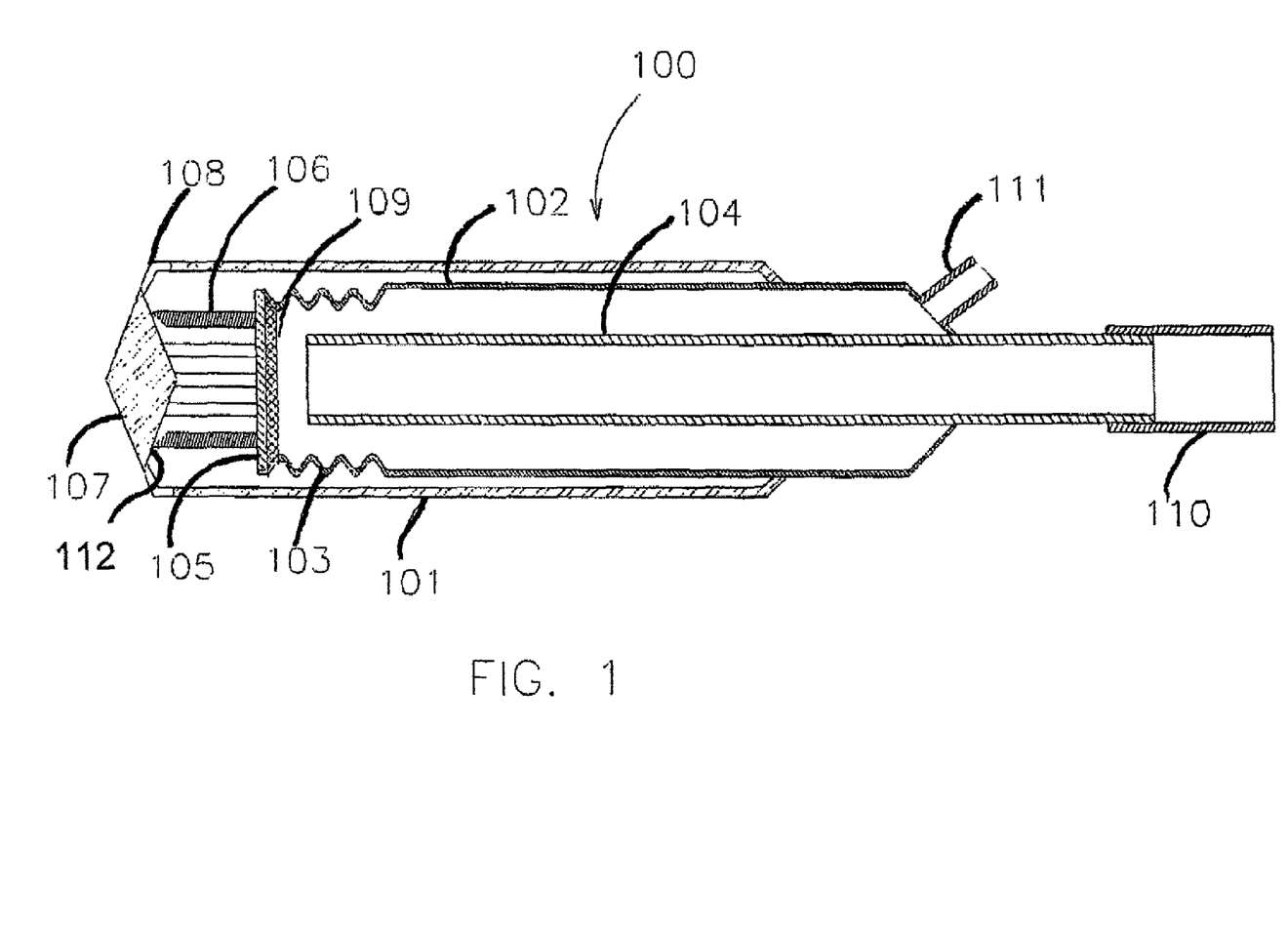
FIG. 1 is a schematic cross section through a cryogenic probe in accordance with a first embodiment of the present invention having solid needles, in its retracted position.

With reference to FIG. 1, a cryogenic probe 100 in accordance with a first embodiment of the present invention is shown. The crypogenic probe 100 is coupled to a cryogenic freezing system (not shown) via connector 110 that serves as an inlet for cryogenic fluid.

A vent conduit 102 and an outlet connection 111 which serve for venting the gaseous phase of the cryogenic fluid after use is also provided.

Figure 2:
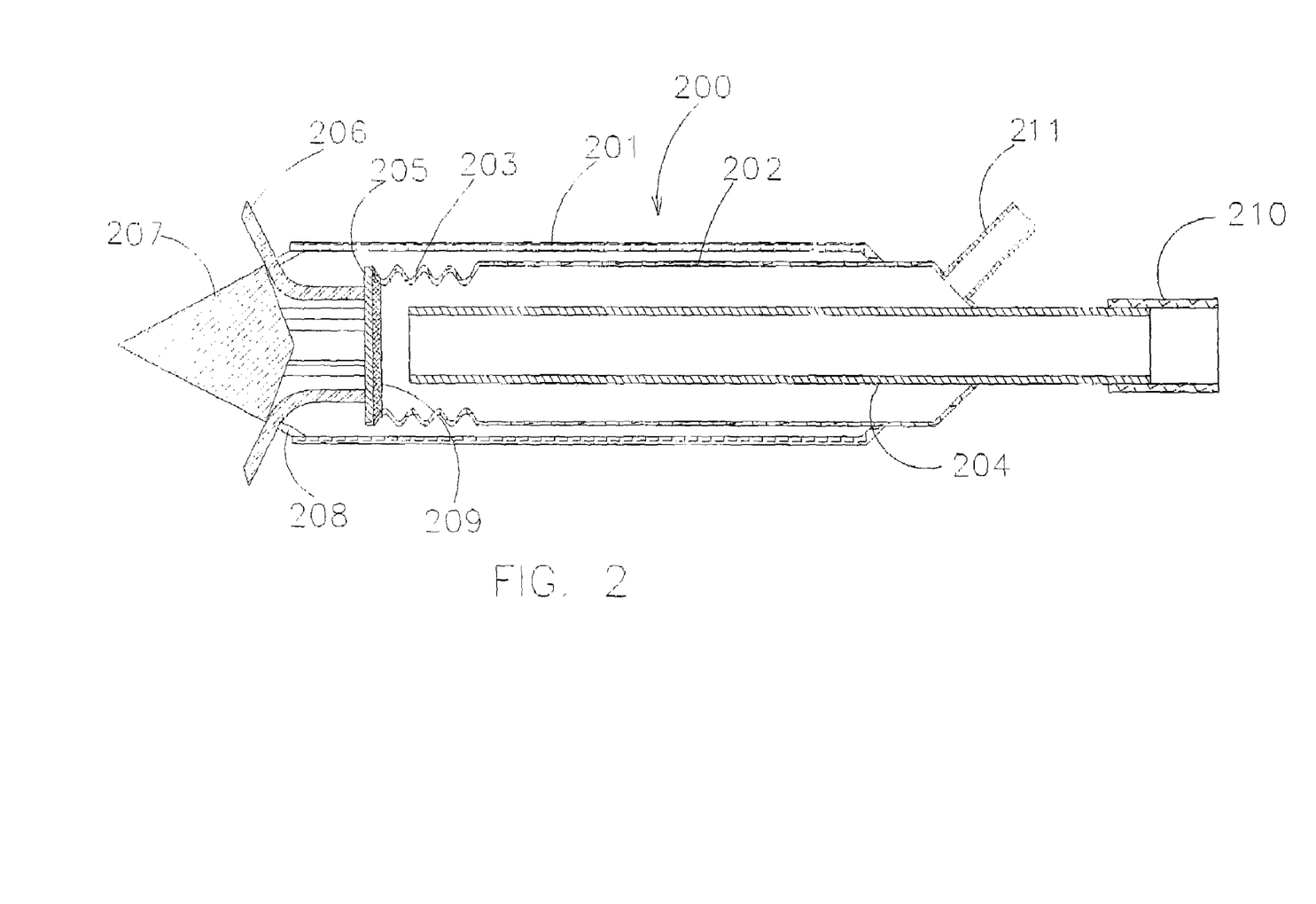
FIG. 2 is a schematic cross section through the cryogenic probe of FIG. 1 in its extended position with extended needles.

The cryogenic probe 100 includes an intermediate lumen 102 that terminates in bellow 103, Bellows 103 are sealed at the distal edge thereof by a face plane 105 to the outer side of which a needle array 106 is appended, such that needle array points forwards, parrallel to axis of the intermediate lumen. Due to the bellows arrangement 103; the needle array 106 may be displaced frontwards and backwards, thereby extended and retracted via openings in cryoprobe tip. The intermediate lumen 102 is coupled to an external lumen 101 at distal end thereof. The external lumen 101 preferably has a high rigidity and is provided with a thermal insulation means. By displacement of bellows 103, the bellows head 105 and the needle array 106 can be displaced-between a retracted position shown in FIG. 1, and an extended position as shown in FIG. 2.

At the distal end of the external lumen 101, a blunt tip 107 is provided, having a deflecting member 112 on inner surface thereof. The needle array 106 comprises one or more needles. Needles 106 extend forwards from the intermediate lumen 102 in a direction substantially parallel to the axis of the intermediate lumen 102, such that if the bellows 103 are expanded, needles 106 are displaced forwards and are deflected sideways and outwards by the deflecting member 112 of blunt tip 107, through apertures 108 set in the wall of the outer lumen 101 at the join between the outer lumen 101 and the blunt tip 107. This results in the needle(s) 106 protruding outwards from the distal end of probe 100, and assuming the extended position shown in FIG. 2. In this manner the needle(s) 106 can provide a cryogenic freezing effect in body tissue situated a larger distance away from tip 107 and the probe shaft, i.e. the outer lumen 101 This increases the effective diameter of the probe 100.

Where, as shown in FIG. 1, a plurality of such needles is arranged in parallel in an array of a regular polygon; circumferentially on the bellow's face plane 105; extension of bellows 103 within the outer lumen 101 results in the needles 105 being splayed out outwards, thereby allowing a cryogenic treatment to be effected over a relatively large volume, having a diameter that is much larger than the effective diameter that can be treated by a conventional cryogenic probe, it being appreciated that the probe 100 is designed for insertion into the body, and should, to minimise damage to tissue during its insertion and removal, be as narrow as possible.

The cryogenic conduit may usefully include an an inner lumen 104 that is terminated at its distal end by connector 110 such that cryogenic fluid entering probe 100 via connector 110 is conveyed down inner lumen 104 to the distal end of the inner lumen 104 to allow a cryogenic fluid to boil on the inner surface of the face plane 105 that is provided with a porous coating 109 with open porosity so that the cryogenic fluid coolingly expands at distal end of the inner lumen 104 within bellows 103, thereby both: displacing face plane 105 forwards and providing a cryogenic freezing effect at the distal end of the probe 100, such that the expansion of the cryogenic gas occurs close to the needle array 106. It should be noted, that a counter-flow heat exchanger, which is requided in this case, is not shown in the drawing.

Typically the flexible needles 106 are all identical, but need not be. In the embodiment of FIG. 1 and 2, the face plane 105 is displacing forwards and the proximal ends of needles 106 are cooled by thermal conductivity from this face plane.

Typically the flexible needles 106 are all identical, but need not be. In the embodiment of FIG. 1 the face plane 105 is-displaced from the retracted position to the extended position by bellows 103, illustrated as being situated right behind the face plane 105 and needle array-106 attached thereto. Expansion of the bellows 103 displaces needles 106 forwards, onto the deflecting member 112, and contraction of bellow 103 displaces the face plane 105 backwards retracting needles 106 attached thereto, providing the probe tip 100 with a small diameter, allowing it to be retracted from the body with minimal difficulty.

The blunt tip 107 of probe 100 is preferably fabricated from a metal having a high thermal conductivity coefficient such as silver, for example. The deflecting member 112 on the inner surface thereof has a shape suitable for smoothly deflecting the flexible needle(s) 106 such as a cone or spherical shape, for example. The inner surface of the face plane 105 may be coated with a porous coating 109 having an open porosity to provide a large surface to encourage cryogenic fluid to boil thereon, providing the cryogenic freezing effect.

FIG. 2 shows the axial section of the cryoprobe with the expandable cryotip in its operation state (where the internal pressure in the internal space of the cryoprobe is significantly higher than the atmospheric pressure). The cryogenic probe 200 comprises three tubular elements: an external shaft 201 with relatively high rigidity, an intervening lumen 202 with a bellows section 203 and a central feeding lumen 204 for delivery of a cryogen.

The needle-wise elements 206 are installed on the outer surface of a face plane 205, which seals the distal section of the intervening lumen 202.

The distal end of the external shaft is closed by a face plane element 207, having a pointed outer surface and an inner surface with a deflecting form. In addition, the distal section of the external shaft 201 is provided with openings 208 for enabling the needle-wise elements 206 to protrude.

The internal surface of the face plane 205 is coated by a porous metal coating 209 with open porosity.

In addition, the proximal end of the central feeding lumen 204 is provided with a pipe connection 210.

In some embodiments, such as that shown in FIGS. 1 and 2, the flexible needle(s) 106 are solid and the proximal end(s) thereof are directly cryogenically cooled, with the distal end(s) thereof being cooled by thermal conduction thereal-ong.

Figure 3:
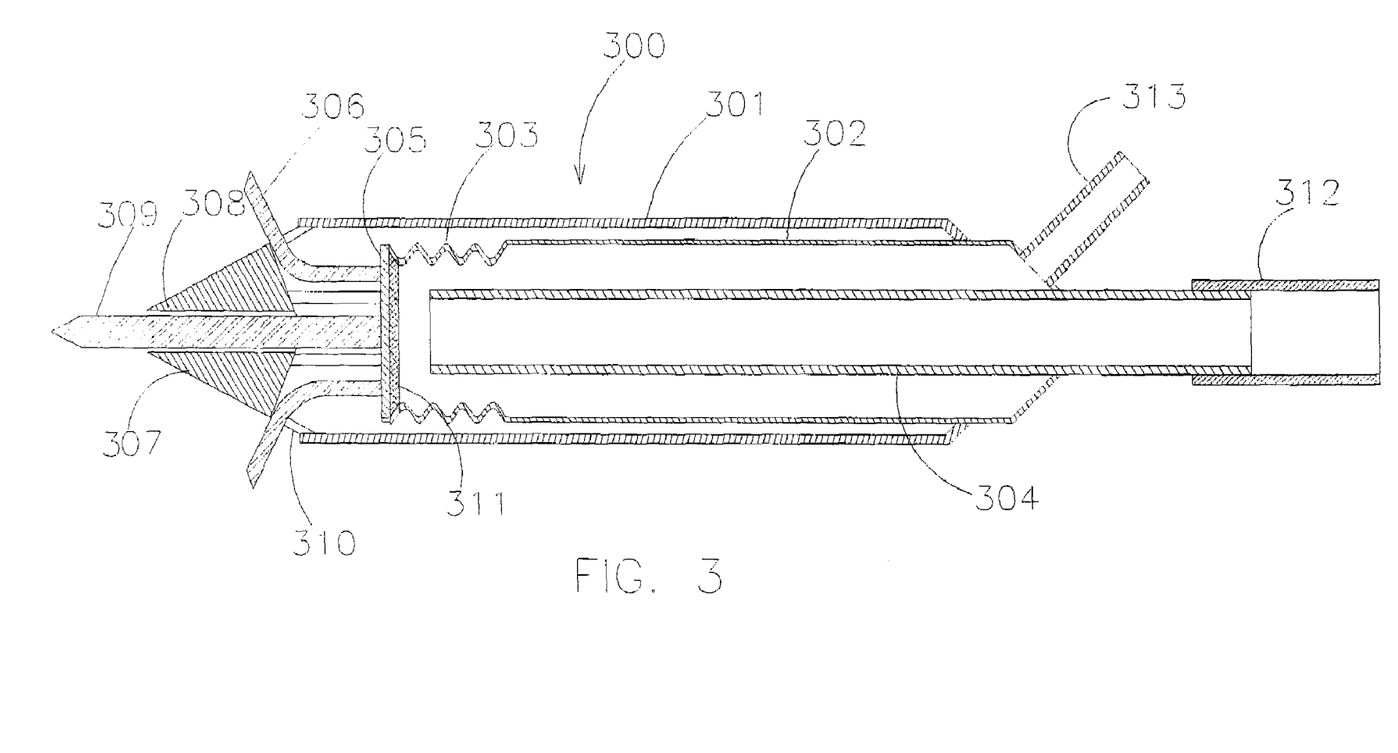
FIG. 3 is a schematic cross section through a cryogenic probe in accordance with a second embodiment of the present invention.

Referring now to FIG. 3, in a second embodiment, mutatis mutandis, the cryogenic probe 300 may additionally include an additional extending needle-wise element 309 and a central hole 308 in the deflecting member 307. The cryoprobe comprises three tubular elements: an external shaft 301 with relatively high rigidity, an intervening lumen 302 with a bellows section 303 and a central feeding lumen 304 for delivery of a cryogen. The peripheral needle-wise elements 306 are installed on the outer side of a face plane 305, which seals the distal section of the intervening lumen 302. The distal end of the external shaft is closed by the deflecting member 307, which is pointed at its surface faced outwards and its surface directed inwards has a deflecting form. There is a central needle wise element 309, which is installed on the outer side of the face plane 305 and positioned in the abovementioned central opening 308 with possibility of protruding from this central opening 308 with change of pressure in the internal space of the intervening lumen 302. In addition, the distal section of the external shaft is provided with openings 310 for protruding the peripheral needle-wise elements 306. The internal surface of the face plane 305 is coated by a porous metal coating 311 with open porosity. The proximal end of the central lumen 304 is provided with an inlet connection 312, and an outlet connection 313 serves for removal of gases from the cryoprobe 300.

Figure 4:
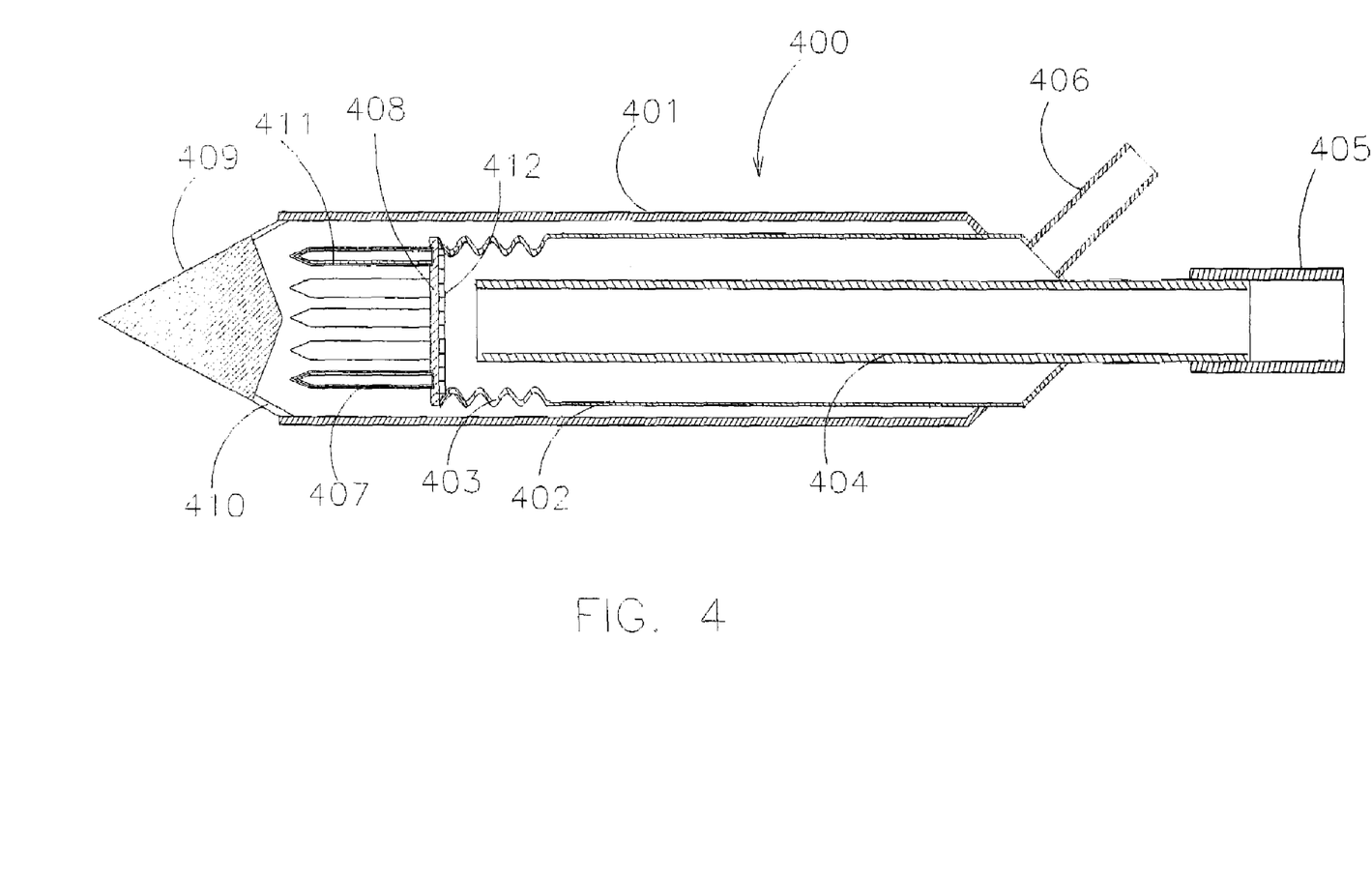
FIG. 4 is a schematic cross section through a cryogenic probe in accordance with a third embodiment of the present invention.

Referring to FIG. 4, in a third embodiment, mutatis mutandis, the flexible needle(s) 407 of probe 400 are sealed hollow needle(s) having closed proximal end(s) and closed distal end(s), the needles serving as heat pipe(s), i.e. they are filled with a cryogenic liquid, and its vapors; their counter-flow in the internal space of the needle allowing effective heat transfer from the proximal section of each needle to its distal section.

The cryoprobe comprises three tubular elements: an external shaft 401 with relatively high rigidity, an intervening lumen 402 with a bellows section 403 and a central feeding lumen 404 with the inlet connection 405 for delivery of a cryogen. The proximal edge of the intervening lumen 402 is sealed with the proximal section of the central feeding lumen 404, and the proximal edge of the external shaft 401 is sealed with the proximal section of the intervening lumen 402. The distal section of the external shaft 401 is provided with opening 410 allowing to protrude needles 407 therethrough. A deflecting member 409 serves for deflecting the needle-wise elements 407 outwards in the process of their displacement forwards.

The proximal section of the intervening lumen 402 is provided with the outlet connection 406 for removal of gases from the internal space of this intervening lumen 402. The needle-wise elements 407 are installed as shown.

Figure 5:
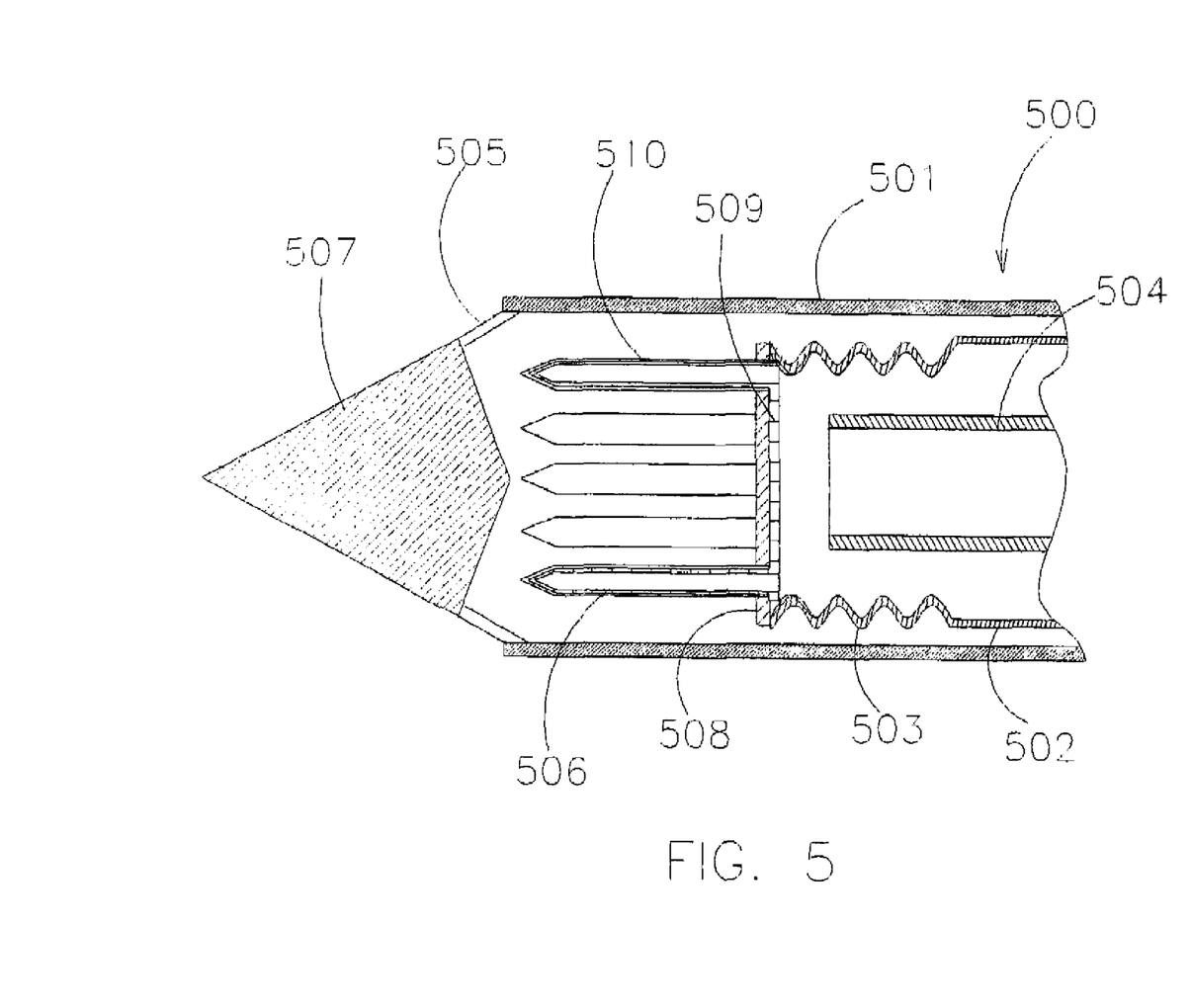
FIG. 5 is a schematic cross section through a cryogenic probe in in accordance with a fourth embodiment of the present invention having hollow needles.

As shown in FIG. 5, in a further embodiment, the enlarged axial section of the distal part of a cryoprobe with the needle-wise elements constructed as open heat pipes. Each needle-wise element 506 is constructed as a heat pipe; the internal walls of this heat pipe is provided with a porous coating 510. The internal surface of the face plane 507 is coated by a porous metal coating 511 with open porosity. The internal spaces of the needle-wise elements 506 is in fluid communication with the internal space of the intervening lumen 502, and the porous metal coatings 510 of these needle-wise elements are in capillary communication with the porous coating 511 of the face plane 507. In such a way, the needle-wise elements 506 are functioning as heat pipes, when the cryogen is delivered via the central feeding lumen 504 on the porous metal coating 511. Again, the needles 510 are displaced to the deflecting member 507 when they are displaced forwards by bellows 503.

In various embodiments, the cryogenic probe may be coupled to a cryogenic cooling system that uses a liquid cryogen such as liquid nitrous oxide, liquid argon or liquid nitrogen, or a gaseous cryogen, such as pressurized gaseous argon or nitrous oxide, for example.

In various embodiments, the cryogenic probe may be coupled to a cryogenic cooling system that uses a liquid cryogen such as liquid nitrous oxide, liquid argon or liquid nitrogen, or a highly pressurized gaseous cryogen which should be expended via an orifice installed on the distal end of the central feeding lumen with its partial liquefying. In the last case, the distal section of the cryoprobe is provided with a counte-flow heat exchanger.

Figure 6:
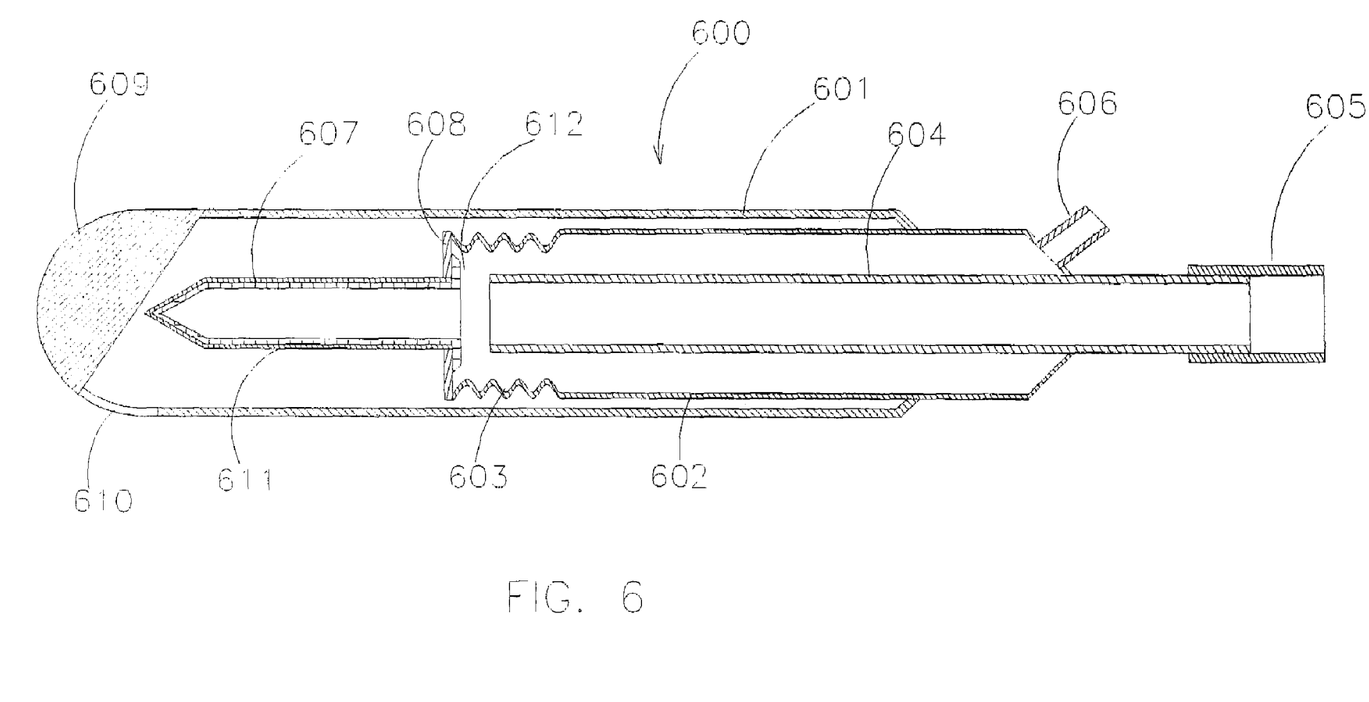
FIG. 6 is a schematic cross section through a cryogenic probe having a single needle probe that extends sideways out of the cylinder when it is displaced forwards by the bellows thereof.

As shown in FIG. 6, in a variant, providing some of the functionality of the embodiments described hereinabove, probe 600 has only one needle 607 provided at the distal end of a face plane 608. The face plane 608 is joined sealingly with bellow 603 and a deflecting member is shaped to deflect needle 620 through an apperture-610 to protrude sideways from shaft 601 of probe 600.

Cryoprobe 600 comprises three tubular elements: the external shaft 601 with relatively high rigidity, an intervening lumen 602 with the bellows section 603 and a central feeding lumen 604 with the inlet connection 605 for delivery of a cryogen. The proximal edge of the intervening lumen 602 is sealed with the proximal section of the central feeding lumen 604, and proximal edge of the external shaft 601 is sealed with the proximal section of the intervening lumen 602.

The proximal section of the intervening lumen 602 is provided with the outlet connection 606 for removal of gases from the internal space of this intervening lumen.

The central needle-wise element 607 is constructed as an open capillary heat pipe; the internal wall of this capillary heat pipe is provided with a porous coating 611.

The internal surface of the face plane 608 is coated with a porous metal coating 612 with open porosity.

The internal spaces of the central needle-wise element 607 is in fluid communication with the internal space of the intervening lumen 602, and the porous metal coating 612 of the central needle-wise element is in capillary communication with the porous coating 611 of the face plane 607.

In this manner, the needle-wise element 607 functions as an open heat pipe, when the cryogen is delivered via the central feeding lumen 604 on the porous metal coating 611.

The cryogenic probes of the present invention may be used in a wide range of surgical applications including, inter alia, to treat cancerous growths, for treating breast cancer, for liver surgery, gynecology, and brainsurgery.

Persons skilled in the art will appreciate that the present invention is not limited to what has been particularly shown and described hereinabove. Rather the scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A cryogenic probe for coupling via a cryogenic conduit to a cryogenic cooling system; said cryogenic probe comprises:

three concentric lumen including an outer lumen ending in a perforated tip having at least one aperture there through and a distal deflecting member;

an intermediate lumen that terminates at distal end thereof in a closed bellows arrangement to which a needle array comprising at least one flexible needle is coupled, the intermediate lumen being sealingly joined by a face plane at proximal end thereof to said outer lumen;

an inner lumen that is open ended and serves to bring a cryogenic medium into close proximity with distal end of the intermediate lumen such that operating pressure delivery of said cryogenic medium in said inner lumen under pressure causes said bellow's arrangement to expand, displacing said at least one needle of the needle array forwards towards said perforated tip, such that said deflecting member deflects said at least one flexible needle of said needle array, sideways and outwards through the at least one aperture, to protrude outwards from the distal end of the cryogenic probe.

2. The cryogenic probe of claim 1 for use in medical applications, such that displacement of the needle array forwards by expansion of the bellows causes the at least one needle of the needle array to be deflected by the deflecting member and to protrude outward from the outer lumen, allowing treatment of tissue in an enlarged volume.

3. The cryogenic probe of claim 1, wherein the needle array comprising a plurality of flexible needles arranged in parallel in a polygon array; said at least one aperture being a plurality of apertures such that displacement of the needle array forwards causes the plurality of flexible needles to splay, by them being deflected sideways and outwards through the apertures to protrude outwards from the distal end of the cryogenic probe.

4. The cryogenic probe of claim 3, wherein the plurality of flexible needles comprises needles that are identical with each other.

5. The cryogenic probe of claim 3, wherein the flexible needles are solid needles, their proximal ends are cryogenically cooled, thereby cooling-their distal ends by thermal conduction.

6. The cryogenic probe of claim 1, wherein at least one flexible needle is a hollow needle having an open proximal end and a closed distal end; the hollow needle being cryogenically cooled by a cryogen therein, in such a way that said hollow needle functions as an open heat pipe.

7. The cryogenic probe of claim 1, wherein at least one flexible needle comprises a hollow needle, and both proximal and distal ends of said at least one needle are closed, such that said hollow needle operates as a closed heat pipe.

8. The cryogenic probe of claim 7, wherein inner surface of said hollow needle is at least partially coated with an open-pore porous metal coating.

9. The cryogenic probe of claim 1, wherein the outer lumen is characterized by at least one of the following list of restrictions: (i) a high rigidity and (ii) a thermal insulation.

10. The cryogenic probe of claim 1, wherein the deflecting member is characterized by at least one of the following list of restrictions: (a) the deflecting member is fabricated from a metal having a high thermal conductivity coefficient; (b) an inner surface of the deflecting member has a shape suitable for smoothly deflecting at least one flexible needle.

11. The cryogenic probe of claim 1, wherein the face plane further comprises an internal porous coating having open pore porosity providing a surface for boiling cryogen thereupon.

12. The cryogenic probe of claim 1, wherein the inner lumen is a conduit provided with a counter-flow heat exchanging means and a distal expansion orifice to allow a high pressure gas to expand into the intermediate lumen and to partial liquefy within the intermediate lumen.

13. The cryogenic probe of claim 1, wherein the cryogenic cooling system uses a liquid cryogen.

14. The cryogenic probe of claim 1, wherein cryogenic probe tip further comprises an additional needle extending outwards from said face plane; said deflecting member having an axial hole therethrough to allow passage of said additional needle.

* * * * *